US012648686B2

(12) United States Patent
Ninomiya

(10) Patent No.: US 12,648,686 B2
(45) Date of Patent: Jun. 9, 2026

(54) BENDING PIECE AND BENDING PORTION OF MEDICAL DEVICE, AND ENDOSCOPE

(71) Applicant: FUJIFILM Corporation, Tokyo (JP)

(72) Inventor: Kota Ninomiya, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 366 days.

(21) Appl. No.: 18/330,370

(22) Filed: Jun. 7, 2023

(65) Prior Publication Data

US 2023/0309803 A1 Oct. 5, 2023

Related U.S. Application Data

(63) Continuation of application No. PCT/JP2021/047236, filed on Dec. 21, 2021.

(30) Foreign Application Priority Data

Jan. 4, 2021 (JP) ................................. 2021-000035

(51) Int. Cl.
 A61B 1/005 (2006.01)
 A61B 1/00 (2006.01)
 A61B 17/29 (2006.01)
(52) U.S. Cl.
 CPC ........ A61B 1/0055 (2013.01); A61B 1/00131 (2013.01); A61B 1/0057 (2013.01); *A61B 17/29* (2013.01)
(58) Field of Classification Search
 CPC . A61B 1/0055; A61B 1/00131; A61B 1/0057; A61B 17/29
 See application file for complete search history.

(56) References Cited

U.S. PATENT DOCUMENTS

2009/0093679 A1 4/2009 Suigetsu et al.
2012/0238805 A1* 9/2012 Iwasaka ............. A61B 1/00098
 600/104

(Continued)

FOREIGN PATENT DOCUMENTS

CN 101541226 9/2009
CN 102670154 9/2012

(Continued)

OTHER PUBLICATIONS

"Search Report of Europe Counterpart Application", issued on Aug. 14, 2024, p. 1-p. 38.

(Continued)

*Primary Examiner* — Michael J Carey
*Assistant Examiner* — Megan Elizabeth Monahan
(74) *Attorney, Agent, or Firm* — JCIPRNET

(57) ABSTRACT

A bending piece of a medical device includes: a ring-shaped piece main body having a peripheral wall part whose cross-section orthogonal to an axial direction is formed in a C-like shape and a slit-shaped opening part extending in the axial direction and provided between one end and the other end of the peripheral wall part in a peripheral direction; a first extension body extending from the peripheral wall part to one side in the axial direction; a second extension body extending from the peripheral wall part to the other side in the axial direction; a connecting shaft provided on the first extension body so as to extend outward in a radial direction orthogonal to the axial direction; and a connecting hole formed in a direction parallel to the connecting shaft, having a shape corresponding to an outer shape of the connecting shaft, and provided in the second extension body.

17 Claims, 8 Drawing Sheets

(56) References Cited

U.S. PATENT DOCUMENTS

| 2015/0164305 | A1* | 6/2015 | Kohno ............... A61B 1/00042 600/149 |
| 2017/0224194 | A1 | 8/2017 | Fujitani et al. |
| 2019/0200843 | A1 | 7/2019 | Lai et al. |
| 2021/0393113 | A1* | 12/2021 | Matthison-Hansen ...................... A61B 1/0055 |

FOREIGN PATENT DOCUMENTS

| CN | 107072494 | 8/2017 |
| JP | H01122702 | 8/1989 |
| JP | H01152604 | 10/1989 |
| JP | H06320473 | 11/1994 |
| JP | 2008253501 | 10/2008 |
| JP | 2009142390 | 7/2009 |
| JP | 2011056074 | 3/2011 |
| JP | 2011156269 | 8/2011 |
| JP | 2012192080 | 10/2012 |
| JP | 2015160078 | 9/2015 |
| JP | 3216707 | 6/2018 |
| WO | 2015108044 | 7/2015 |

OTHER PUBLICATIONS

"International Search Report (Form PCT/ISA/210) of PCT/JP2021/047236", mailed on Mar. 8, 2022, with English translation thereof, pp. 1-5.
"International Preliminary Report on Patentability (Form PCT/IPEA/409) of PCT/JP2021/047236", completed on Jul. 19, 2022, with English translation thereof, pp. 1-6.
"Notice of Reasons for Refusal of Japan Counterpart Application", issued on May 16, 2025, with English translation thereof, p. 1-p. 10.
"Office Action of China Counterpart Application", issued on Jul. 29, 2025, with English translation thereof, p. 1-p. 18.
"Office Action of China Counterpart Application", issued on Feb. 13, 2026, with English translation thereof, p. 1-p. 10.

* cited by examiner

BENDING PIECE AND BENDING PORTION OF MEDICAL DEVICE, AND ENDOSCOPE

CROSS-REFERENCE TO RELATED APPLICATIONS

The present application is a Continuation of PCT International Application No. PCT/JP2021/047236 filed on Dec. 21, 2021 claiming priority under 35 U.S.C § 119(a) to Japanese Patent Application No. 2021-000035 filed on Jan. 4, 2021. Each of the above applications is hereby expressly incorporated by reference, in its entirety, into the present application.

BACKGROUND OF THE INVENTION

1. Field of the Invention

The present invention relates to a bending piece and a bending portion of a medical device, and an endoscope.

2. Description of the Related Art

An endoscope, which is one of medical devices, includes a bending portion in an insertion part, and the bending portion is configured by connecting a plurality of bending pieces in an axial direction of the insertion part.

For example, an endoscope disclosed in JP1989-152604U (JP-H01-152604U) includes a bending portion in which a plurality of bending pieces arranged along an axial direction are connected by rivets so as to be rotationally movable. In addition, an endoscope disclosed in JP2011-156269A includes a bending portion in which a plurality of joint pieces are connected along an insertion direction of an insertion part so as to be rotationally movable. In the endoscope of JP2011-156269A, one joint piece and the other joint piece adjacent to each other in the insertion direction are connected by two rivets located 180° apart from each other in a circumferential direction so as to be rotationally movable in two directions.

As described above, the conventional endoscope employs, as the structure of the bending portion, a structure in which two adjacent bending pieces (joint pieces) are connected by rivets.

SUMMARY OF THE INVENTION

However, the conventional endoscope using the rivet in assembling the bending portion has the following problem.

That is, in a case of assembling the bending portion, first, respective rivet insertion holes formed in two adjacent bending pieces (joint pieces) are aligned and overlapped with each other, the rivet is inserted into the overlapped rivet insertion hole, and then the rivet is clinched using a dedicated tool, so that the two adjacent bending pieces are connected to each other. Since it is necessary to perform such connecting work for the number of bending pieces, there is a problem that the assembly of the bending portion is time-consuming.

The present invention has been made in view of such circumstances, and an object of the present invention is to provide a bending piece and a bending portion of a medical device, and an endoscope capable of improving the assemblability of the bending portion.

In order to solve the above-described problem, a bending piece of a medical device of an aspect of the present invention comprises: a ring-shaped piece main body having a peripheral wall part of which a cross-section orthogonal to an axial direction is formed in a C-like shape and a slit-shaped opening part extending in the axial direction and provided between one end and the other end of the peripheral wall part in a peripheral direction; a first extension body extending from the peripheral wall part to one side in the axial direction; a second extension body extending from the peripheral wall part to the other side in the axial direction; a connecting shaft provided on the first extension body and provided so as to extend outward in a radial direction orthogonal to the axial direction; and a connecting hole formed in a direction parallel to the connecting shaft and having a hole shape corresponding to an outer shape of the connecting shaft, the connecting hole being provided in the second extension body.

According to one form of the bending piece of a medical device of the aspect of the present invention, it is preferable that the first extension body is disposed with an offset at a position that does not overlap with the second extension body in a case in which the first extension body and the second extension body are projected onto a plane orthogonal to the axial direction.

According to one form of the bending piece of a medical device of the aspect of the present invention, it is preferable that the second extension body has a second extension body outer peripheral surface formed along a surface extending from an outer peripheral surface of the peripheral wall part.

According to one form of the bending piece of a medical device of the aspect of the present invention, it is preferable that the connecting shaft has a connecting shaft distal end surface formed along the surface extending from the outer peripheral surface of the peripheral wall part.

According to one form of the bending piece of a medical device of the aspect of the present invention, it is preferable that a pair of wire insertion holes formed by penetrating through the peripheral wall part and the second extension body along the axial direction are further provided.

According to one form of the bending piece of a medical device of the aspect of the present invention, it is preferable that, in a case in which the pair of wire insertion holes and the connecting shaft are viewed from the axial direction, the pair of wire insertion holes are disposed at positions on both sides of the connecting shaft interposed therebetween.

According to one form of the bending piece of a medical device of the aspect of the present invention, it is preferable that a space part for pipe line member disposition, which is a space part for disposing a pipe line member along the axial direction and communicates with the opening part, is defined inside the peripheral wall part, and that the piece main body has a pipe line member holding part for holding the pipe line member disposed in the space part for pipe line member disposition.

According to one form of the bending piece of a medical device of the aspect of the present invention, it is preferable that the pipe line member holding part has a holding claw portion provided at at least one end part of both end parts of the peripheral wall part, which is located on both sides of the opening part interposed therebetween, and protruding to an opening part side.

According to one form of the bending piece of a medical device of the aspect of the present invention, it is preferable that the peripheral wall part has an inner wall surface that defines the space part for pipe line member disposition, that the inner wall surface includes a pair of facing surfaces facing each other and provided on both sides of the space part for pipe line member disposition interposed therebetween, and that the pipe line member holding part has a holding groove portion provided on at least one of the pair of facing surfaces.

According to one form of the bending piece of a medical device of the aspect of the present invention, it is preferable that the peripheral wall part has an inner wall surface that defines the space part for pipe line member disposition, and that the piece main body has a restricting member that restricts movement of the pipe line member disposed in the space part for pipe line member disposition in the radial direction orthogonal to the axial direction, the restricting member being provided on the inner wall surface.

According to one form of the bending piece of a medical device of the aspect of the present invention, it is preferable that the bending piece is made of a resin.

In order to solve the above-described problem, a bending portion of a medical device of another aspect of the present invention comprises: a plurality of the bending pieces of the aspect of the present invention, in which one bending piece and the other bending piece adjacent to each other are connected to each other by inserting a connecting shaft of the one bending piece into a connecting hole of the other bending piece so as to be rotationally movable about an axis of the connecting shaft.

According to one form of the bending portion of a medical device of the aspect of the present invention, it is preferable that a space part for pipe line member disposition, which is a space part for disposing a pipe line member along the axial direction and communicates with the opening part, is defined inside the peripheral wall part, and that the pipe line member is disposed over the respective space parts for pipe line member disposition of the plurality of connected bending pieces.

According to one form of the bending portion of a medical device of the aspect of the present invention, it is preferable that a part of the pipe line member is disposed outward of a virtual outer shape formed by a surface extending from an outer peripheral surface of the peripheral wall part toward an opening part side.

According to one form of the bending portion of a medical device of the aspect of the present invention, it is preferable that outer peripheral surfaces of the plurality of connected bending pieces are covered with a covering member.

According to one form of the bending portion of a medical device of the aspect of the present invention, it is preferable that the covering member is tightly fitted to the outer peripheral surfaces of the plurality of connected bending pieces.

According to one form of the bending portion of a medical device of the aspect of the present invention, it is preferable that a pair of wire insertion holes formed by penetrating through the peripheral wall part and the second extension body along the axial direction are further provided, and that wires are inserted into the pair of wire insertion holes of each of the plurality of connected bending pieces.

In order to solve the above-described problem, an endoscope of still another aspect of the present invention comprises: the bending portion of a medical device of the aspect of the present invention.

According to the present invention, it is possible to improve assemblability of the bending portion.

DESCRIPTION OF THE PREFERRED EMBODIMENTS

Hereinafter, embodiments of a bending piece and a bending portion of a medical device, and an endoscope of an embodiment of the present invention will be described with reference to the accompanying drawings.

Figure 1:
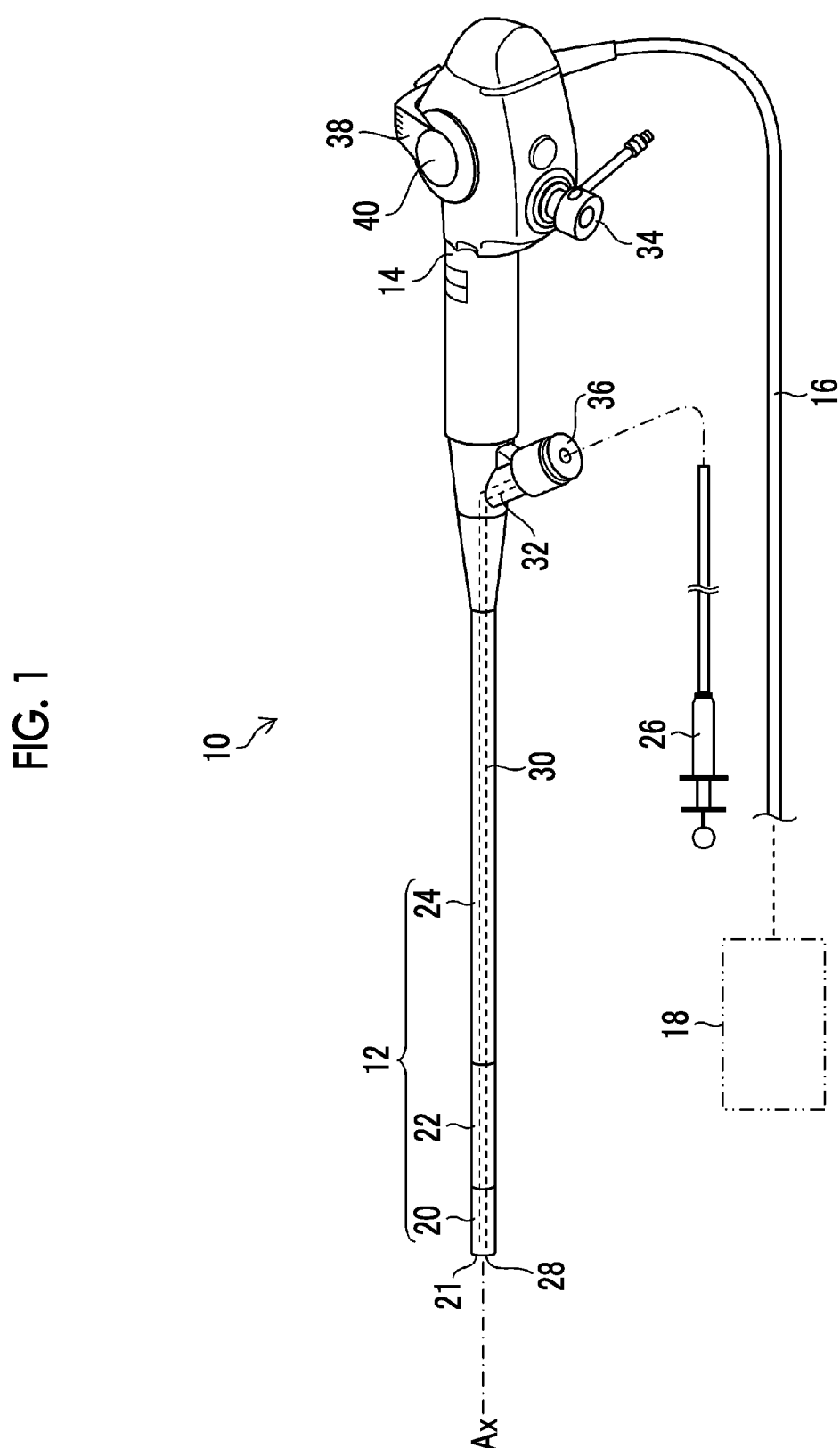
FIG. 1 is an overall configuration view of an endoscope according to an embodiment of the present invention.

FIG. 1 is an overall configuration view of an endoscope 10 according to the embodiment of the present invention. The endoscope 10 shown in FIG. 1 is, for example, a bronchoscope to be inserted into the trachea and comprises an insertion part 12 to be inserted into the trachea, a handpiece operation part 14 consecutively provided at the proximal end part of the insertion part 12, and a universal cord 16 connected to the handpiece operation part 14. The universal cord 16 is connected to a processor device, a light source device, and the like (not shown) via a connector 18 indicated by an alternate long and two short dashes line in FIG. 1.

The insertion part 12 has a major axis direction Ax from the distal end side toward the proximal end side thereof and is provided with a distal end rigid portion 20, a bending portion 22 that is bendable, and a soft portion 24 having flexibility in this order from the distal end side toward the proximal end side. The bending portion 22 is an example of a bending portion of the embodiment of the present invention.

A treatment tool outlet port 28, which is an outlet of a treatment tool 26, such as a forceps, is provided on a distal end surface 21 of the distal end rigid portion 20. In addition, the above-described distal end surface 21 is provided with an observation window and an illumination window (not shown) at predetermined positions. An image sensor (not shown) is disposed on the back side (proximal end side) of the observation window, and an optical fiber cable (not shown) is disposed on the back side (proximal end side) of the illumination window. A signal line of the image sensor and the optical fiber cable are each inserted from the distal end rigid portion 20 into the bending portion 22, the soft portion 24, the handpiece operation part 14, the universal cord 16, and the connector 18 and are connected to the above-described processor device and the light source device, respectively.

A treatment tool channel 30 for inserting the treatment tool 26 is provided inside the insertion part 12. The distal end of the treatment tool channel 30 is connected to the treatment tool outlet port 28, and the proximal end is connected to a channel opening portion 32 of the handpiece operation part 14. In addition, a disposable type forceps valve 36 through which the treatment tool 26 can be inserted is attachably and detachably mounted on the channel opening portion 32. The treatment tool channel 30 is used not only as a pipe line for inserting the treatment tool 26, but also as a pipe line for suctioning body fluid, such as blood, or solid matter, such as bodily waste, from the treatment tool outlet port 28. The treatment tool channel 30 has flexibility and is an example of a pipe line member of the embodiment of the present invention.

In addition, a suction channel (not shown) branched from the treatment tool channel 30 is disposed inside the handpiece operation part 14, and the suction channel is connected to a suction button 34 of the handpiece operation part 14. The suction button 34 is connected to a suction pump (not shown) disposed outside the handpiece operation part 14, and the suction channel and the suction pump communicate with each other or are blocked from each other through a pressing operation of the suction button 34 or a release of the pressing operation.

Figure 2:
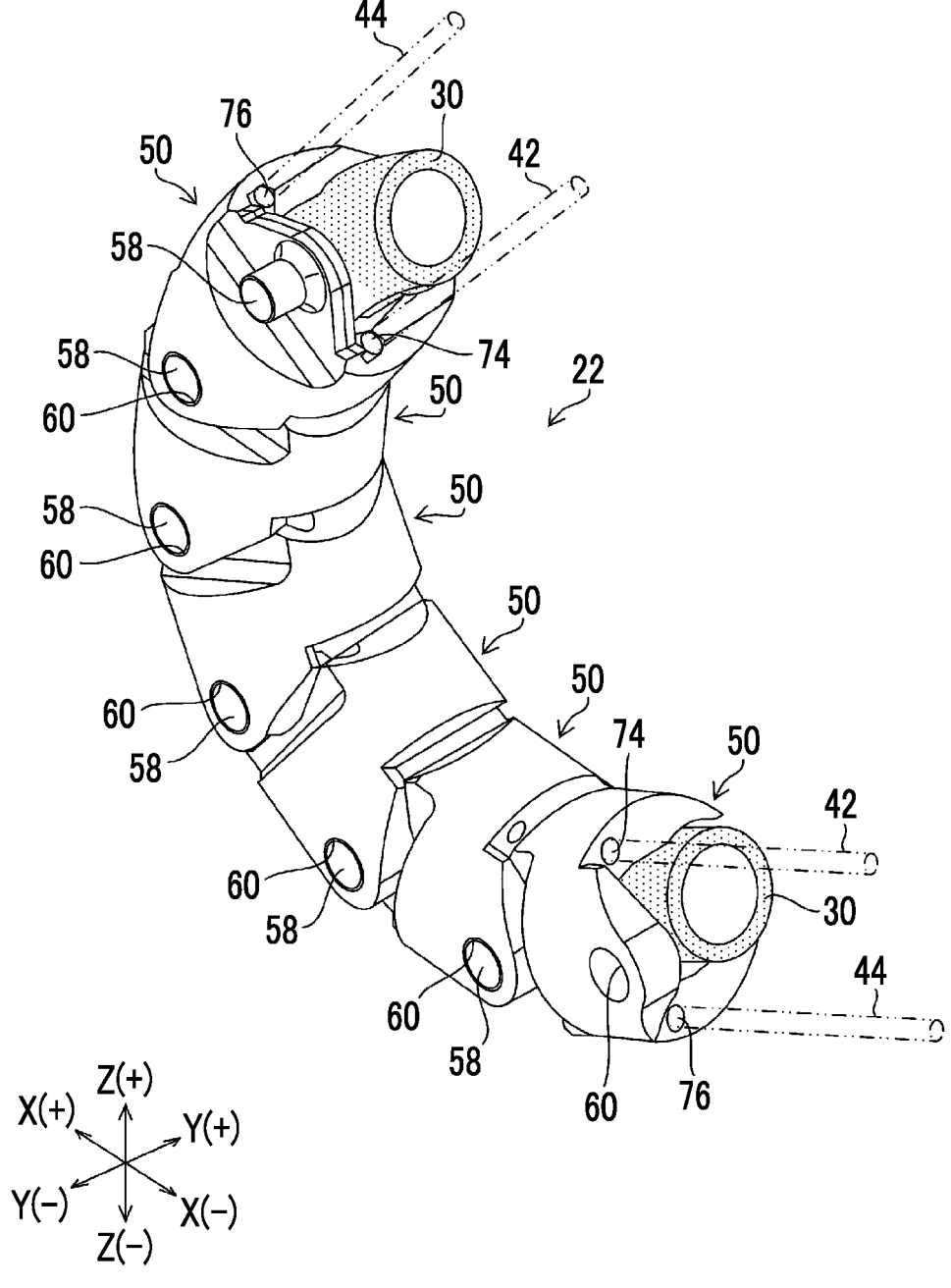
FIG. 2 is a perspective view showing a structure of a bending portion.

In addition, an angle lever 38 for performing a bending operation of the bending portion 22 is disposed in the handpiece operation part 14. The angle lever 38 is provided so as to be rotationally movable about a rotational movement shaft 40 with respect to the handpiece operation part 14. The angle lever 38 and the bending portion 22 are connected to each other via two wires 42 and 44 (see FIG. 2) for bending operations, which are disposed inside the insertion part 12. The angle lever 38 operates the wires 42 and 44 to be pushed and pulled through the rotational movement operation, whereby the bending portion 22 shown in FIG. 2 is bent in two directions (for example, an up-down direction). Here, FIG. 2 is a perspective view showing the structure of the bending portion 22 and shows a form in which the bending portion 22 is bent upward.

In the present specification, descriptions are given using a three-dimensional Cartesian coordinate system, that is, three-axis directions (an X-axis direction, a Y-axis direction, and a Z-axis direction) orthogonal to each other. That is, in a case in which a direction in which the distal end surface 21 of the distal end rigid portion 20 is directed upward by the bending operation of the angle lever 38 when the distal end rigid portion 20 is viewed from the handpiece operation part 14 is defined as an upper direction, the upper direction is defined as a Z (+) direction, and a lower direction, which is opposite to the upper direction, is defined as a Z (−) direction. In addition, in that case, a front direction (a direction on the distal end side of the major axis direction Ax of the insertion part 12) is defined as an X (+) direction, and a rear direction (a direction on the proximal end side of the major axis direction Ax of the insertion part 12) is defined as an X (−) direction. Further, in that case, a right direction is defined as a Y (+) direction and a left direction is defined as a Y (−) direction. The X-axis direction including the X (+) direction and the X (−) direction, and the axial direction of the axis P of a bending piece 50 (see FIG. 3) constituting bending portion 22, which will be described below, are parallel to the major axis direction Ax in a case in which the insertion part 12 is linearly disposed. In addition, the configuration of the handpiece operation part 14 is not limited to the aspect shown in FIG. 1. By providing a pair of angle knobs instead of the angle lever 38 and performing the rotation operation of the pair of angle knobs, the bending operation of the bending portion 22 in the up-down direction and the left-right direction may be performed. In addition, by providing an air/water supply button on the handpiece operation part 14 and operating the air/water supply button, a gas, such as air, a cleaning liquid, or the like may be supplied to the distal end rigid portion 20.

Next, the structure of the bending portion 22 shown in FIG. 2 will be described with reference to the perspective view of the bending piece 50 shown in FIG. 3. The bending portion 22 shown in FIG. 2 comprises a plurality of the bending pieces 50 shown in FIG. 3 and is configured by connecting these bending pieces 50 to each other along the axial direction of the axis P. The bending piece 50 is an example of a bending piece of the embodiment of the present invention.

Figures 4A, 4B, 4C, 4D, 4E:
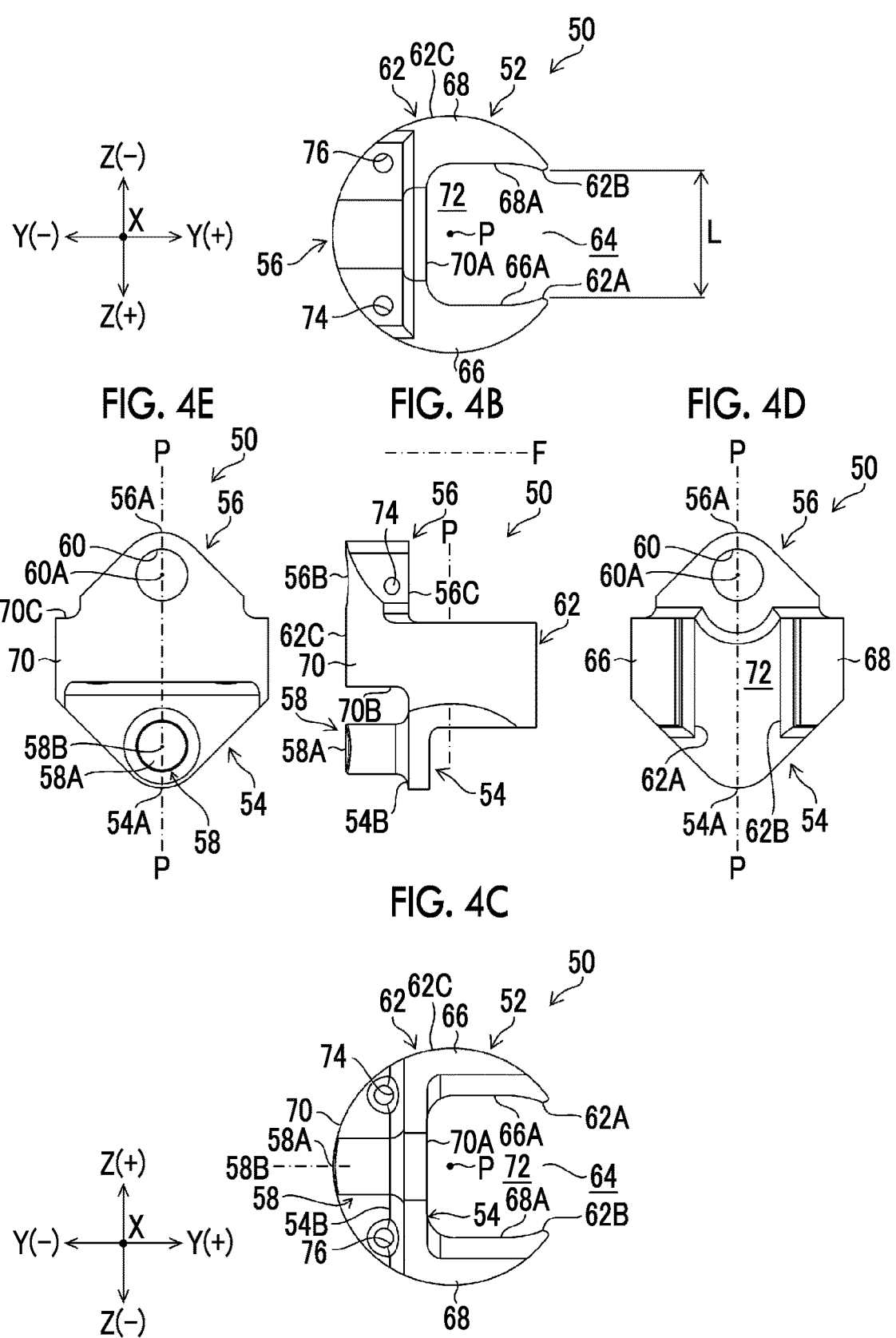
FIGS. 4A to 4E are five-view views of the bending piece as viewed from five directions.

Hereinafter, a configuration of the bending piece 50 will be described with reference to FIGS. 4A to 4E. FIGS. 4A to 4E show five-view views of the bending piece 50 as viewed from five directions, in which FIG. 4A is a front view (a view of the bending piece 50 as viewed from a distal end rigid portion 20 side), FIG. 4B is a plan view (a view of the bending piece 50 as viewed from a Z (+) direction side), FIG. 4C is a rear view (a view of the bending piece 50 as viewed from a soft portion 24 side), FIG. 4D is a right side view (a view of the bending piece 50 as viewed from a Y (+) direction side), and FIG. 4E is a left side view (a view of the bending piece 50 as viewed from a Y (−) direction side).

Figure 3:
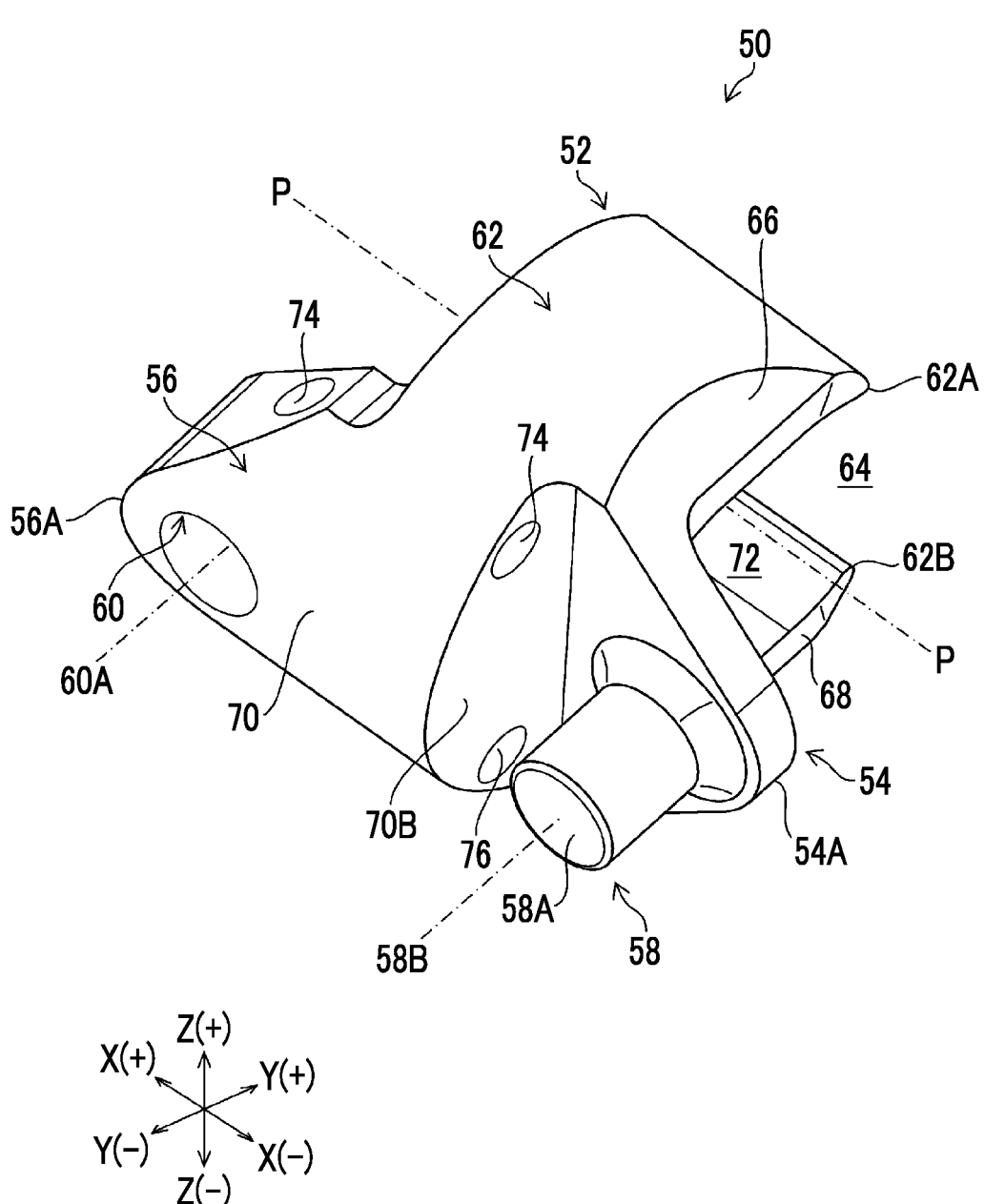
FIG. 3 is a perspective view of a bending piece that constitutes the bending portion.

As shown in FIGS. 3 to 4E, the bending piece 50 comprises a piece main body 52, a first extension body 54, a second extension body 56, a connecting shaft 58, and a connecting hole 60.

As shown in FIGS. 4A and 4C, the piece main body 52 is configured in a ring shape having a peripheral wall part 62 of which a cross-section orthogonal to the axial direction of the axis P is formed in a C-like shape, and a slit-shaped opening part 64 provided between one end 62A and the other end 62B of the peripheral wall part 62 in a peripheral direction and extending in the axial direction of the axis P. Here, the axis P is defined as a central axis of the piece main body 52 for description.

Specifically, the peripheral wall part 62 of the piece main body 52 has an outer shape based on a substantially columnar shape, and an outer peripheral surface 62C of the peripheral wall part 62 is configured in a C-like shape in a case in which the peripheral wall part 62 is viewed from the axial direction (hereinafter, also referred to as "X-axis direction") of the axis P. In addition, the peripheral wall part 62 has substantially triangular arm portions 66 and 68 disposed on the Z (+) direction side and the Z (−) direction side with the axis P interposed therebetween, and a substantially fan-shaped proximal portion 70 disposed opposite to the opening part 64 with the axis P interposed therebetween. The arm portions 66 and 68 are provided so as to extend from the proximal portion 70 in the Y (+) direction, and the one end 62A and the other end 62B described above are formed at end parts of the arm portions 66 and 68 on the Y (+) direction side, respectively. In the piece main body 52 configured as described above, in a case in which the piece main body 52 is viewed from the X-axis direction, the piece main body 52 has a substantially rectangular space part 72 defined by respective inner wall surfaces 66A, 68A, and 70A of the arm portions 66 and 68 and of the proximal portion 70, and the space part 72 communicates with the opening part 64 in the Y (+) direction. The space part 72 functions as a space part for pipe line member disposition of the embodiment of the present invention.

The C-like shape defining the shape of the outer peripheral surface 62C of the peripheral wall part 62 includes not only the C-like shape but also a shape similar to the C-like shape, such as a U-like shape and a J-like shape. That is, the C-like shape refers to a shape in which the opening part 64 and the peripheral wall part 62 are continuously disposed in the peripheral direction of the space part 72 so as to surround the inner space part 72.

The space part 72 provided in the piece main body 52 is formed by penetrating through the axis P so that the size of the space part 72 is ensured as the space part for pipe line member disposition, and built-in members of the endoscope, such as the treatment tool channel 30 shown in FIG. 2, the signal line (not shown) of the image sensor, and the optical fiber cable (not shown), are housed in the space part 72.

Further, the one end 62A and the other end 62B of the peripheral wall part 62 shown in FIGS. 4A to 4E each protrude toward an opening part 64 side. That is, the one end 62A and the other end 62B described above are configured as holding claw portions of a pipe line member holding part of the embodiment of the present invention. Further, a distance (opening width) L between the one end 62A and the other end 62B in the Z-axis direction is set to be shorter than the diameter of the treatment tool channel 30. In the bending piece 50 having such one end 62A and the other end 62B, an outer peripheral surface 30A of the treatment tool channel 30 housed in the space part 72 comes into contact with the one end 62A and the other end 62B, whereby the treatment tool channel 30 is held in the space part 72 and is prevented from falling off from the space part 72 via the opening part 64.

In the bending piece 50 of the present example, although both the one end 62A and the other end 62B are configured as holding claw portions, the present invention is not limited thereto, and at least one end part of the one end 62A or the other end 62B may be configured as the above-described holding claw portion. For example, the one end 62A may be configured as the holding claw portion and the other end 62B may be configured to be flush with the inner wall surface 68A of the arm portion 68, or the other end 62B may be configured as the holding claw portion and the one end 62A may be configured to be flush with the inner wall surface 66A of the arm portion 66. In addition, in a case of housing the treatment tool channel 30 in the space part 72, the treatment tool channel 30 may be disposed by being inserted along the axis P or may be disposed by being inserted from the opening part 64 into the space part 72. That is, by pushing the treatment tool channel 30 from the opening part 64 in the radial direction orthogonal to the axial direction of the treatment tool channel 30, the treatment tool channel 30 may be disposed by being inserted into the space part 72. Here, as the treatment tool channel 30, a case in which the cross-sectional shape of the treatment tool channel 30 in a direction orthogonal to the axial direction is a perfect circle is described as an example.

The first extension body 54 is provided so as to extend from the peripheral wall part 62 to the soft portion 24 side (the proximal end side of the bending piece 50), which is one side in the X-axis direction. Specifically, as shown in FIG. 4B, the first extension body 54 is provided so as to extend from a surface 70B on the soft portion 24 side of the proximal portion 70 to the soft portion 24 side in parallel with the axis P. In addition, as shown in FIG. 4E, the outer shape of the first extension body 54 is based on a substantially isosceles triangle, and a distal end 54A of the first extension body 54 is disposed at a position overlapping with the axis P in a case in which the first extension body 54 is viewed from the Y-axis direction.

The second extension body 56 is provided so as to extend from the peripheral wall part 62 to the distal end rigid portion 20 side (the distal end side of the bending piece 50), which is the other side in the X-axis direction. Specifically, as shown in FIG. 4E, the second extension body 56 is provided so as to extend from a surface 70C on the distal end rigid portion 20 side of the proximal portion 70 to the distal end rigid portion 20 side in parallel with the axis P. In addition, the outer shape of the second extension body 56 is based on a substantially isosceles triangle, and a distal end 56A of the second extension body 56 is disposed at a position overlapping with the axis P in a case in which the second extension body 56 is viewed from the Y-axis direction. Further, as shown in FIG. 4B, the second extension body 56 has an outer peripheral surface 56B formed along a surface extending from the outer peripheral surface 62C of the peripheral wall part 62. The outer peripheral surface 56B corresponds to a second extension body outer peripheral surface of the embodiment of the present invention.

The connecting shaft 58 is provided on the first extension body 54 and is provided so as to extend outward in the radial direction orthogonal to the X-axis direction. Specifically, the connecting shaft 58 is configured in a columnar shape and, as shown in FIGS. 4B and 4C, is provided so as to extend from an outer end surface 54B of the first extension body 54 in the Y (−) direction. In addition, the connecting shaft 58 has a distal end surface 58A formed along the surface extending from the outer peripheral surface 62C of the peripheral wall part 62. The distal end surface 58A corresponds to a connecting shaft distal end surface of the embodiment of the present invention. As a result, as shown in FIG. 4C, in a case in which the connecting shaft 58 and the peripheral wall part 62 are viewed from the X-axis direction, the connecting shaft 58 has an axial length from the outer end surface 54B to the outer peripheral surface 62C in the Y-axis direction. Further, as shown in FIG. 4E, in a case in which the first extension body 54 is viewed from the Y-axis direction, an axis 58B, which is the central axis of the connecting shaft 58, is disposed at a position overlapping with the axis P.

The connecting hole 60 is provided in the second extension body 56. The connecting hole 60 is formed in a direction parallel to the connecting shaft 58 and has a hole shape corresponding to the outer shape of the connecting shaft 58. Specifically, the connecting hole 60 is provided so as to penetrate through the second extension body 56 in the Y-axis direction. Further, as shown in FIG. 4E, in a case in which the second extension body 56 is viewed from the Y-axis direction, an axis 60A, which is the central axis of the connecting hole 60, is disposed at a position overlapping with the axis P. As a result, in a case in which the first extension body 54 and the second extension body 56 are viewed from the Y-axis direction, the axis 58B of the connecting shaft 58 and the axis 60A of the connecting hole 60 are disposed on the axis P. The connecting shaft 58 of adjacent bending piece 50 is inserted into the connecting hole 60 at the time of assembling the bending portion 22. With this, as shown in FIG. 4C, two adjacent bending pieces 50, one and the other, are connected so as to be rotationally movable about the axes 58B and 60A at positions opposite to the opening part 64 with the axis P interposed therebetween.

Further, as shown in FIG. 4B, in a case in which the first extension body 54 and the second extension body 56 are projected onto a virtual plane F orthogonal to the X-axis direction, the first extension body 54 of the bending piece 50 is disposed with an offset at a position that does not overlap with the second extension body 56. Specifically, in a case in which the first extension body 54 and the second extension body 56 are viewed from the X-axis direction, the outer end surface 54B of the first extension body 54 is disposed closer to the axis P than an inner end surface 56C of the second extension body 56. By disposing the first extension body 54 with an offset in this manner, it is possible to set a longer axial length of the connecting shaft 58 protruding from the outer end surface 54B of the first extension body 54.

In addition, as shown in FIG. 3, the bending piece 50 has a pair of wire insertion holes 74 and 76 formed by penetrating through the peripheral wall part 62 and the second extension body 56 along the X-axis direction. The wire 42 (see FIG. 2) is inserted into the wire insertion hole 74, and the wire 44 (see FIG. 2) is inserted into the wire insertion hole 76. As described above, the proximal end side of these wires 42 and 44 is connected to the angle lever 38 of FIG. 1, and the distal end side is connected to, for example, the bending piece 50 located at the most distal end of the bending portion 22.

As shown in FIG. 4C, the pair of wire insertion holes 74 and 76 are disposed at positions on both sides of the connecting shaft 58 interposed therebetween in a case in which the pair of wire insertion holes 74 and 76 and the connecting shaft 58 are viewed from the X-axis direction. Specifically, the pair of wire insertion holes 74 and 76 are disposed at positions on both sides of the connecting shaft 58 interposed therebetween in a direction (Z-axis direction) orthogonal to the axial direction (Y-axis direction) of the connecting shaft 58. Further, the disposition positions of the wire insertion holes 74 and 76 need only be positions on both sides of the connecting shaft 58 interposed therebetween, but the wire insertion holes 74 and 76 of the present example are provided at symmetrical positions with the connecting shaft 58 interposed therebetween in the Z-axis direction, as shown in FIG. 4C. The above is the configuration of the bending piece 50.

The bending piece 50 configured as described above is, as an example, a resin molded product formed of a resin material, such as polyacetal. The bending piece 50 is not limited to being made of a resin and may be made of, for example, a metal, such as stainless steel. However, from the viewpoint of manufacturing the bending piece 50, it is preferable that the bending piece 50 is made of a resin that can be easily manufactured by injection molding or the like.

Returning to FIG. 2, the bending portion 22 is assembled by performing the assembly work of the bending pieces 50 adjacent to each other, that is, inserting the connecting shaft 58 of one bending piece 50 into the connecting hole 60 of the other bending piece 50, for all the bending pieces 50. After that, the wires 42 and 44 are inserted into the pair of wire insertion holes 74 and 76 of each of the plurality of connected bending pieces 50, respectively, and the distal end side of the wires 42 and 44 is connected to the bending piece 50 located at the most distal end of the bending portion 22, so that the bending portion 22 with wires 42 and 44 is assembled.

Figure 5:
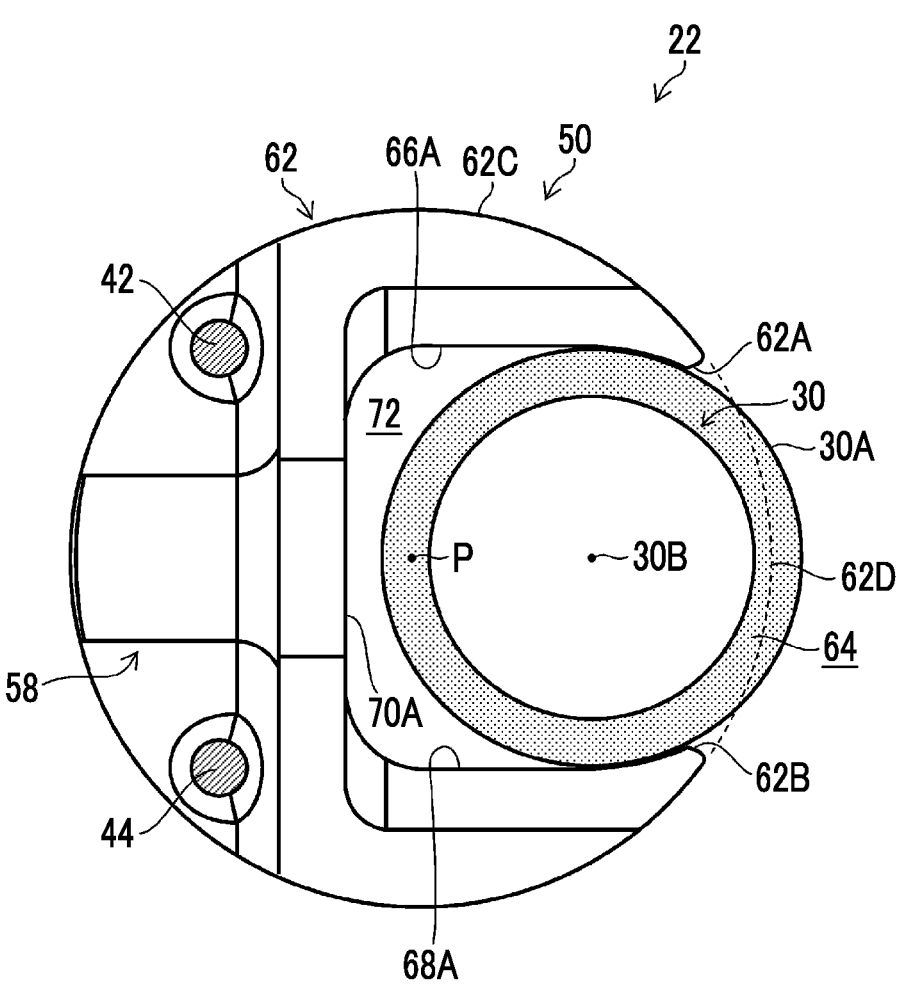
FIG. 5 is an enlarged view of a main part showing a disposition position of a pipe line member with respect to the bending portion.
Figure 5:
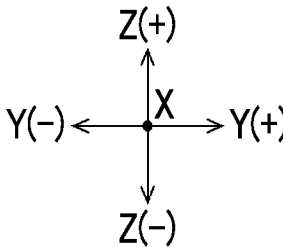

FIG. 5 is an enlarged view of a main part of the bending piece 50 as viewed from an X (−) direction side of the bending portion 22 with the wires 42 and 44 shown in FIG. 2 and is a view showing a disposition position of the treatment tool channel 30 with respect to the bending portion 22. According to FIGS. 2 and 5, the treatment tool channel 30 is disposed along the axial direction of the axis P over the respective space parts 72 of the plurality of connected bending pieces 50. Further, FIG. 5 shows a form in which a part of the outer peripheral surface 30A of the treatment tool channel 30 is disposed outward of a virtual outer shape 62D formed by a surface extending from the outer peripheral surface 62C of the peripheral wall part 62 toward the opening part 64 side (Y (+) direction side).

In addition, in the treatment tool channel 30 shown in FIG. 5, an axis 30B, which is the central axis thereof, is disposed closer to the Y (+) direction with respect to the axis P, and the outer peripheral surface 30A thereof is in contact with the one end 62A and the other end 62B of the peripheral wall part 62. In order to dispose the treatment tool channel 30 at such a position, in the endoscope 10 of the present example, for example, the treatment tool outlet port 28 with respect to the distal end surface 21 (see FIG. 1) is disposed closer to the Y (+) direction with respect to the axis P similarly to the axis 30B of the treatment tool channel 30.

Figure 6:
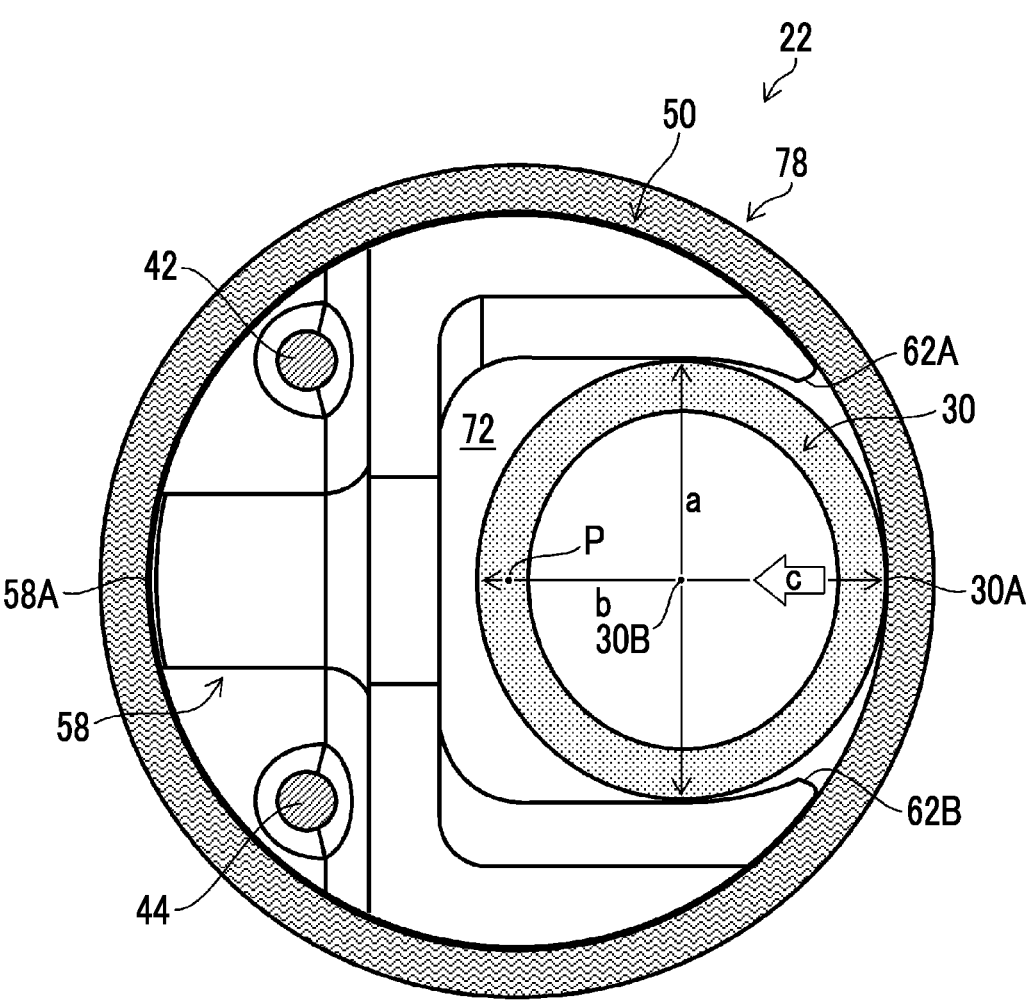
FIG. 6 is an explanatory view of a main part in which the bending portion shown in FIG. 5 is covered with a rubber tube.
Figure 6:
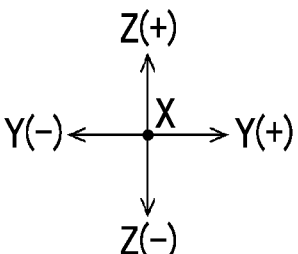

FIG. 6 is an enlarged view of a main part of the bending portion 22 showing that the outer peripheral surfaces of the plurality of connected bending pieces 50 are covered with a rubber tube 78 constituting an outer cover. The rubber tube 78 is an example of a covering member of the embodiment of the present invention. The covering member is not limited to the rubber tube 78, but it is preferable to employ an elastic rubber tube because the covering member can be tightly fitted to the outer peripheral surfaces of the plurality of connected bending pieces 50. Examples of the rubber tube 78 include a resin-based elastomer tube, such as fluororubber or silicone rubber. It is not essential that the covering member is tightly fitted to the outer peripheral surface of the bending piece 50, but it is preferable to tightly fit the covering member to the outer peripheral surface of the bending piece 50 as in the present example because the diameter of the bending portion 22 can be reduced.

The bending piece 50, the bending portion 22, and the endoscope 10 configured as described above have the following effects.

That is, as shown by the bending piece 50 of FIGS. 4A to 4E, since the bending portion 22 can be assembled by providing the connecting shaft 58 on the first extension body 54 of the piece main body 52, providing the connecting hole 60 having a hole shape corresponding to the outer shape of the connecting shaft 58 and parallel to the connecting shaft 58 in the second extension body of the piece main body 52, and inserting the connecting shaft 58 into the connecting hole 60, the bending portion 22 can be easily assembled. As a result, with the bending piece 50, the bending portion 22, and the endoscope 10 of the present embodiment, the assemblability of the bending portion 22 is improved.

Further, with the bending piece 50 of the present example, as shown in FIGS. 4A to 4E, in a case in which the first extension body 54 and the second extension body 56 are projected onto the virtual plane F orthogonal to the X-axis direction, the first extension body 54 is disposed with an offset at a position that does not overlap with the second extension body, so that the axial length of the connecting shaft 58 (a fitting length with the connecting hole 60) can be made longer. As a result, the two adjacent bending pieces 50, one and the other, can be stably connected to each other. In addition, in a case in which the plurality of bending pieces 50 are connected to form the bending portion 22, between the bending pieces 50 adjacent to each other, the first extension body 54 of one bending piece 50 and the second extension body 56 of the other bending piece 50 can be prevented from interfering with each other when the bending operation of the bending portion 22 is performed.

Further, with the bending piece 50 of the present example, since the second extension body 56 has the outer peripheral surface 56B formed along the surface extending from the outer peripheral surface 62C of the peripheral wall part 62, the rubber tube 78 can be tightly fitted to the outer peripheral surfaces of the plurality of connected bending pieces 50 (see FIG. 6).

Further, with the bending piece 50 of the present example, since the connecting shaft 58 has the distal end surface 58A formed along the surface extending from the outer peripheral surface 62C of the peripheral wall part 62, the axial length of the connecting shaft 58 can be maximized while achieving the above-described tight fitting (see FIG. 6). As a result, two adjacent bending pieces 50, one and the other, can be more stably connected to each other.

Further, with the bending piece 50 of the present example, since the pair of wire insertion holes 74 and 76 are disposed at positions on both sides of the connecting shaft 58 interposed therebetween in a case in which the pair of wire insertion holes 74 and 76 and the connecting shaft 58 are viewed from the X-axis direction, the force generated by the pushing and pulling operation of the wires 42 and 44, that is, the force for bending the bending portion 22 can be effectively transmitted to the bending piece 50. As a result, the bending portion 22 can be smoothly bent. In a case in which the wire insertion holes 74 and 76 of the present example are provided at symmetrical positions with the connecting shaft 58 interposed therebetween, the bending portion 22 can be bent in the upper direction and the lower direction with the same force, so that the bending operation feeling of the bending portion 22 can be made constant.

Further, with the bending piece 50 of the present example, since the peripheral wall part 62 has the one end 62A and the other end 62B that function as the holding claw portions, the treatment tool channel 30 disposed in the space part 72 can be prevented from falling off from the space part 72 via the opening part 64.

Meanwhile, in the bending portion 22 of the present example, as shown in FIG. 5, the outer peripheral surfaces of the plurality of connected bending pieces 50 are covered with the rubber tube 78 in a state in which a part of the outer peripheral surface 30A of the treatment tool channel 30 is disposed outward of the virtual outer shape 62D (see FIG. 6). The rubber tube 78 is tightly fitted to the outer peripheral surfaces of the plurality of connected bending pieces 50.

The bending portion 22 configured as described above has the following effects.

That is, as shown in FIG. 6, a part of the outer peripheral surface 30A of the treatment tool channel 30 disposed outward of the opening part 64 is pressed to the axis P side as indicated by an arrow c by the elastic force (diameter-reducing force) of the rubber tube 78. As a result, the treatment tool channel 30 is deformed from a state in which the cross-sectional shape thereof is a perfect circle into an elliptical shape having a major axis a in the Z-axis direction and a minor axis b in the Y-axis direction. The treatment tool channel 30, which is deformed into such a shape, receives a force in the Z-axis direction from the bending portion 22 in a case in which the bending portion 22 is bent in the Z-axis direction, but the treatment tool channel 30 is deformed into an elliptical shape having the major axis a in the Z-axis direction so as to counteract that force. As a result, since the treatment tool channel 30 is less likely to collapse in the direction of the major axis a when the bending portion 22 is bent, it is possible to suppress the occurrence of kink that occurs when the bending portion 22 is bent.

Figure 7A:
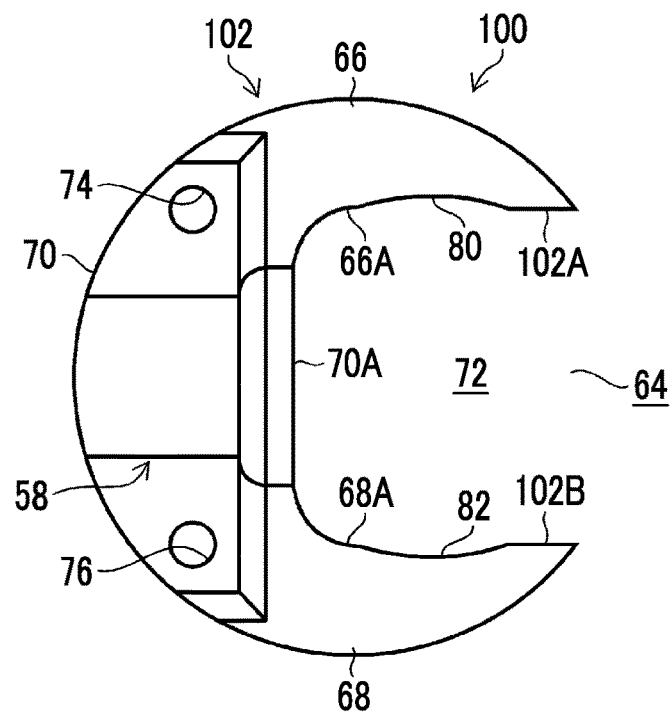
FIGS. 7A and 7B are explanatory views showing some other modification examples of a pipe line member holding part.
Figure 7B:
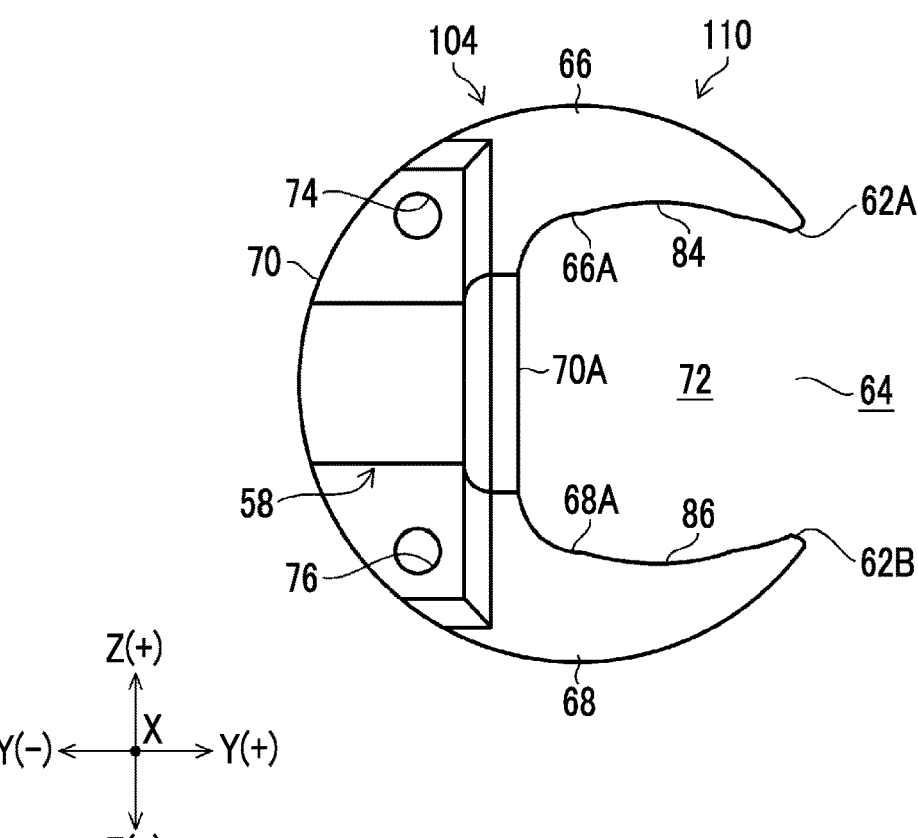

Hereinafter, some modification examples of the pipe line member holding part will be described with reference to FIGS. 7A and 7B. FIG. 7A is an explanatory view of a bending piece 100 showing a first modification example of the pipe line member holding part, and FIG. 7B is an explanatory view of a bending piece 110 showing a second modification example of the pipe line member holding part. When describing the bending pieces 100 and 110 of FIGS.

7A and 7B, the same or similar members as those of the bending piece 50 described with reference to FIGS. 2 to 6 are designated by the same reference numerals, and the description thereof will be omitted.

With the bending piece 100 shown in FIG. 7A, a peripheral wall part 102 has the inner wall surfaces 66A, 68A, and 70A defining the space part 72. In addition, the inner wall surfaces 66A, 68A, and 70A include the inner wall surfaces 66A and 68A facing each other and provided on both sides of the space part 72 interposed therebetween. The inner wall surfaces 66A and 68A correspond to a pair of facing surfaces of the embodiment of the present invention. The pipe line member holding part has holding groove portions 80 and 82 on the inner wall surfaces 66A and 68A, respectively.

Further, in the bending piece 100, one end 102A and the other end 102B of the peripheral wall part 102 are not configured as the holding claw portions protruding toward the opening part 64 side, and the one end 102A is formed on the same surface as the inner wall surface 66A, and the other end 102B is formed on the same surface as the inner wall surface 68A.

That is, the bending piece 100 shown in FIG. 7A has a form in which the holding groove portions 80 and 82 are provided as the pipe line member holding part, but the holding claw portion is not provided. Even in such a bending piece 100, the outer peripheral surface 30A of the treatment tool channel 30 (see FIG. 5) is accommodated in the holding groove portions 80 and 82, whereby the treatment tool channel 30 can be held in the space part 72 of the bending piece 100. In addition, in FIG. 7A, the bending piece 100 in which the holding groove portions 80 and 82 are formed on both the inner wall surfaces 66A and 68A is shown, but the present invention is not limited thereto, and one of the inner wall surfaces 66A and 68A need only have the holding groove portion.

In the bending piece 110 shown in FIG. 7B, a peripheral wall part 104 has the inner wall surfaces 66A, 68A, and 70A defining the space part 72. In addition, the inner wall surfaces 66A, 68A, and 70A include the inner wall surfaces 66A and 68A facing each other and provided on both sides of the space part 72 interposed therebetween. The inner wall surfaces 66A and 68A correspond to the pair of facing surfaces of the embodiment of the present invention. The pipe line member holding part has holding groove portions 84 and 86 on the inner wall surfaces 66A and 68A.

Further, in the bending piece 110, the one end 62A and the other end 62B of the peripheral wall part 104 are configured as the holding claw portions protruding toward the opening part 64 side.

That is, the bending piece 110 shown in FIG. 7B has a form in which the holding groove portions 84 and 86 are provided as the pipe line member holding part and the one end 62A and the other end 62B, which are holding claw portions, are provided. Even in such a bending piece 110, the outer peripheral surface 30A of the treatment tool channel 30 (see FIG. 5) is accommodated in the holding groove portions 84 and 86 and is brought into contact with the one end 62A and the other end 62B, whereby the treatment tool channel 30 can be held in the space part 72 of the bending piece 110. In addition, in FIG. 7B, the bending piece 110 in which the holding groove portions 84 and 86 are formed on both the inner wall surfaces 66A and 68A is shown, but the present invention is not limited thereto, and one of the inner wall surfaces 66A and 68A need only have the holding groove portion. Further, similarly, both the one end 62A and the other end 62B are configured as the holding claw portions, but one end part need only be configured as the holding claw portion.

Here, for example, as shown in FIG. 5, the treatment tool channel 30 held in the space part 72 of the bending piece 50 receives a force in an arrow c direction by the contractile force of the rubber tube 78 shown in FIG. 6. At this time, in order to suppress the kink of the treatment tool channel 30 and to reliably deform the treatment tool channel 30 into the elliptical shape shown in FIG. 6, it is desirable to restrict the treatment tool channel 30 from moving in the radial direction (Y (−) direction) orthogonal to the axial direction of the axis 30B of the treatment tool channel 30.

In that respect, some forms of a restricting member that restricts the above-described movement will be described with reference to FIGS. 8A to 8D.

Figure 8A:
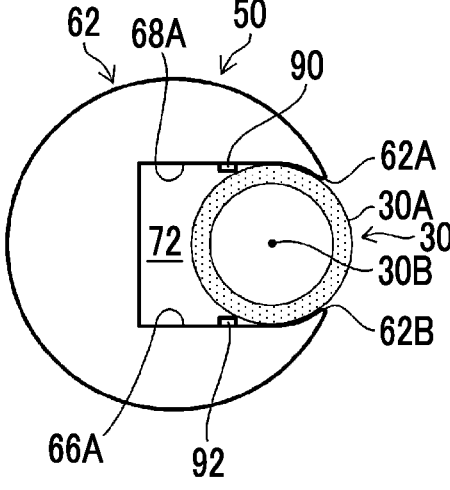
FIGS. 8A to 8D are explanatory views showing some forms of a bending piece provided with a restricting member.

A first form shown in FIG. 8A is a form in which restricting members 90 and 92 are provided on the bending piece 50 shown in FIG. 5. In FIG. 8A, the bending piece 50 shown in FIG. 5 is simply shown. In the first form, the restricting members 90 and 92 are provided on the inner wall surfaces 66A and 68A of the peripheral wall part 62 and come into contact with the outer peripheral surface 30A of the treatment tool channel 30 disposed in the space part 72, thereby restricting the treatment tool channel 30 from moving in the radial direction (Y (−) direction). Specifically, the restricting members 90 and 92 are configured as protruding portions that protrude from the inner wall surfaces 66A and 68A toward the space part 72. Further, the restricting members 90 and 92 are disposed at a predetermined distance interval in the Z-axis direction, and the positions in the Y-axis direction are the same. That is, the restricting members 90 and 92 are disposed by being spaced apart from each other on a straight line parallel to the Z-axis direction. As a result, it is possible to stably restrict the treatment tool channel 30 from moving in the radial direction (Y (−) direction). In the first form, the bending piece 50 in which the restricting members 90 and 92 are provided on both the inner wall surfaces 66A and 68A is shown, but the present invention is not limited thereto, and one of the inner wall surfaces 66A and 68A need only have the restricting member.

Figure 8C:
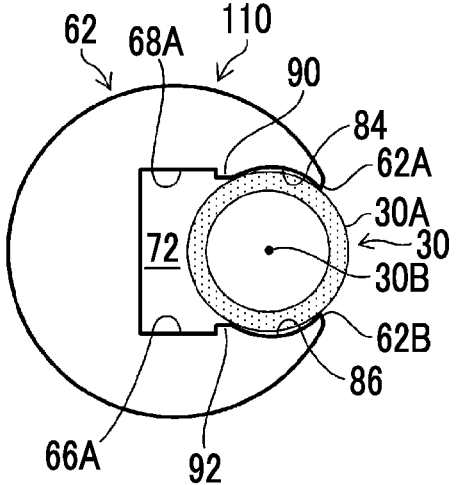
Figure 8B:
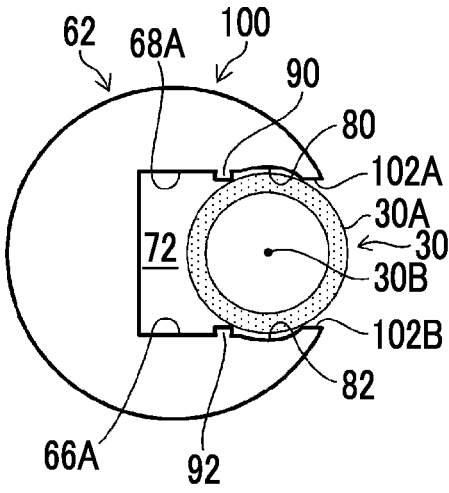

A second form shown in FIG. 8B is a form in which the restricting members 90 and 92 are provided on the bending piece 100 shown in FIG. 7A, and the bending piece 100 shown in FIG. 7A is simply shown. Even in the second form in which the restricting members 90 and 92 are provided on the bending piece 100 having the holding groove portions 80 and 82, it is possible to stably restrict the treatment tool channel 30 from moving in the radial direction (Y (−) direction).

A third form shown in FIG. 8C is obtained by providing the restricting members 90 and 92 on the bending piece 110 shown in FIG. 7B, and the bending piece 110 shown in FIG. 7B is simply shown. Even in the third form in which the restricting members 90 and 92 are provided on the bending piece 110 having the holding groove portions 80 and 82 and the one end 62A and the other end 62B, which are the holding claw portions, it is possible to stably restrict the treatment tool channel 30 from moving in the radial direction (Y (−) direction).

Figure 8D:
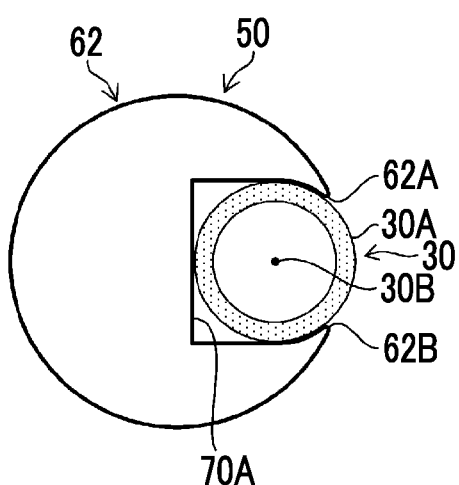
Figure 8D:
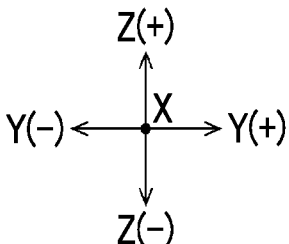

A fourth form shown in FIG. 8D is obtained by bringing the inner wall surface 70A of the bending piece 50 shown in FIG. 5 closer to an axis 30B side of the treatment tool channel 30 than in the form of FIG. 5 and by bringing the outer peripheral surface 30A of the treatment tool channel 30 into contact with the inner wall surface 70A to make the inner wall surface 70A function as the restricting member. Even in such a fourth form, it is possible to stably restrict the treatment tool channel 30 from moving in the radial direction (Y (−) direction).

Although an example in which the bending piece of the medical device according to the present invention is applied to the bending portion of the bronchoscope has been described above, the technology of the present invention is not limited to a bending portion of the bronchoscope and can also be applied to, for example, bending portions of other endoscopes, such as the colonoscopes or enteroscopes. Further, the bending piece and the bending portion according to the present invention are not limited to the endoscope and can also be applied to, for example, a bending portion of a treatment tool (for example, see WO2019/172318A), which is one of the medical devices. Furthermore, the present invention may be subject to some improvements or modifications within the scope that does not deviate from the gist of the present invention.

EXPLANATION OF REFERENCES

10: endoscope
12: insertion part
14: handpiece operation part
16: universal cord
18: connector
20: distal end rigid portion
21: distal end surface
22: bending portion
24: soft portion
26: treatment tool
28: treatment tool outlet port
30: treatment tool channel
30A: outer peripheral surface
30B: axis
32: channel opening portion
34: suction button
36: forceps valve
38: angle lever
40: rotational movement shaft
42: wire
44: wire
50: bending piece
52: piece main body
54: first extension body
54A: distal end
54B: outer end surface
56: second extension body
56A: distal end
56B: outer peripheral surface
56C: inner end surface
58: connecting shaft
58A: distal end surface
58B: axis
60: connecting hole
60A: axis
62: peripheral wall part
62A: one end
62B: other end
62C: outer peripheral surface
62D: virtual outer shape
64: opening part
66: arm portion
66A: inner wall surface
68: arm portion
68A: inner wall surface

15

70: proximal portion
70A: inner wall surface
70B: surface
70C: surface
72: space part
74: wire insertion hole
76: wire insertion hole
78: rubber tube
80: holding groove portion
82: holding groove portion
84: holding groove portion
86: holding groove portion
90: restricting member
92: restricting member
100: bending piece
102: peripheral wall part
102A: one end
102B: other end
104: peripheral wall part
110: bending piece
P: axis
F: virtual plane
What is claimed is:

1. A bending piece of a medical device, comprising:
a ring-shaped piece main body having a peripheral wall part of which a cross-section orthogonal to an axial direction is formed in a C-like shape and a slit-shaped opening part extending in the axial direction and provided between one end and the other end of the peripheral wall part in a peripheral direction;
a first extension body extending from the peripheral wall part to one side in the axial direction;
a second extension body extending from the peripheral wall part to the other side in the axial direction;
a connecting shaft provided on the first extension body and provided so as to extend outward in a radial direction orthogonal to the axial direction; and
a connecting hole formed in a direction parallel to the connecting shaft and having a hole shape corresponding to an outer shape of the connecting shaft, the connecting hole being provided in the second extension body; and
a pair of wire insertion holes formed within the peripheral wall part and the second extension body along the axial direction,
wherein a number of the first extension body is one and a number of the second extension body is one.

2. The bending piece of the medical device according to claim 1,
wherein the first extension body is disposed with an offset at a position that does not overlap with the second extension body in a case in which the first extension body and the second extension body are projected onto a plane orthogonal to the axial direction.

3. The bending piece of the medical device according to claim 1,
wherein the second extension body has a second extension body outer peripheral surface formed along a surface extending from an outer peripheral surface of the peripheral wall part.

4. The bending piece of the medical device according to claim 3,
wherein the connecting shaft has a connecting shaft distal end surface formed along the surface extending from the outer peripheral surface of the peripheral wall part.

5. The bending piece of the medical device according to claim 1,

wherein, in a case in which the pair of wire insertion holes and the connecting shaft are viewed from the axial direction, the pair of wire insertion holes are disposed at positions on both sides of the connecting shaft.

6. The bending piece of the medical device according to claim 1,
wherein a space part for pipe line member disposition, which is the space part for disposing a pipe line member along the axial direction and communicates with the slit-shaped opening part, is defined inside the peripheral wall part, and
the ring-shaped piece main body has a pipe line member holding part for holding the pipe line member disposed in the space part for the pipe line member disposition.

7. The bending piece of the medical device according to claim 6,
wherein the pipe line member holding part has a holding claw portion provided at, at least one end part of both end parts of the peripheral wall part, which is located on both sides of the slit-shaped opening part interposed therebetween, and protruding to an opening part side.

8. The bending piece of the medical device according to claim 6,
wherein the peripheral wall part has an inner wall surface that defines the space part for the pipe line member disposition,
the inner wall surface includes a pair of facing surfaces facing each other and provided on both sides of the space part for the pipe line member disposition interposed therebetween, and
the pipe line member holding part has a holding groove portion provided on at least one of the pair of facing surfaces.

9. The bending piece of the medical device according to claim 6,
wherein the peripheral wall part has an inner wall surface that defines the space part for the pipe line member disposition, and
the ring-shaped piece main body has a restricting member that restricts movement of the pipe line member disposed in the space part for the pipe line member disposition in the radial direction orthogonal to the axial direction, the restricting member being provided on the inner wall surface.

10. The bending piece of the medical device according to claim 1,
wherein the bending piece is made of a resin.

11. A bending portion of the medical device, comprising:
a plurality of bending pieces, wherein each of the plurality of bending pieces comprise the bending piece according to claim 1,
wherein one bending piece and the other bending piece adjacent to each other are connected to each other by inserting the connecting shaft of the one bending piece into the connecting hole of the other bending piece so as to be rotationally movable about an axis of the connecting shaft.

12. The bending portion of the medical device according to claim 11, wherein a space part for pipe line member disposition, which is a space part for disposing a pipe line member along the axial direction and communicates with the slit-shaped opening part, is defined inside the peripheral wall part, and
the pipe line member is disposed over the space part for pipe line member disposition of the plurality of bending pieces.

13. The bending portion of the medical device according to claim 12, wherein a part of the pipe line member is disposed outward of a virtual outer shape formed by a surface extending from an outer peripheral surface of the peripheral wall part toward an opening part side.

14. The bending portion of the medical device according to claim 13, wherein outer peripheral surfaces of the plurality of bending pieces are covered with a covering member.

15. The bending portion of the medical device according to claim 14, wherein the covering member is tightly fitted to the outer peripheral surfaces of the plurality of bending pieces.

16. The bending portion of the medical device according to claim 11, further comprising:

wherein wires are inserted into the pair of wire insertion holes of each of the plurality of bending pieces.

17. An endoscope comprising:

the bending portion of the medical device according to claim 11.

\*  \*  \*  \*  \*